United States Patent [19]

Shanel

[11] Patent Number: 4,512,742
[45] Date of Patent: Apr. 23, 1985

[54] HOLDER FOR RUBBER DENTAL DAM

[76] Inventor: Kathleen A. Shanel, 428 Park Blvd., Glen Ellyn, Ill. 60137

[21] Appl. No.: 85,252

[22] Filed: Oct. 16, 1979

Related U.S. Application Data

[63] Continuation of Ser. No. 790,567, Apr. 25, 1977, Pat. No. 4,215,477.

[51] Int. Cl.³ .............................................. A61C 5/12
[52] U.S. Cl. ................................................... 433/136
[58] Field of Search ........................ 433/136, 137, 138

[56] References Cited

U.S. PATENT DOCUMENTS

| | | | |
|---|---|---|---|
| 296,992 | 4/1884 | Moffitt | 433/137 |
| 682,308 | 9/1901 | Young | 433/136 |
| 702,394 | 6/1902 | Beall | 433/137 |
| 1,207,756 | 12/1916 | Holmes | 433/137 |
| 3,406,452 | 10/1968 | McConville | 433/136 |
| 4,215,477 | 8/1980 | Shanel | 433/136 |

OTHER PUBLICATIONS

"Ostby Rubber Dam Frame" ad, Hygienic pamphlet, 1962.
"Orthodontics Principles and Practice", by T. M. Graber, pp. 77 and 228.

Primary Examiner—John J. Wilson
Attorney, Agent, or Firm—Laff, Whitesel, Conte & Saret

[57] ABSTRACT

A facial frame surrounds a greater arcuate portion of the patient's face, than has been used heretofore. The frame includes fasteners for a dental dam, preferably made from a thin rubber sheet. The frame has fasteners which are oriented so that the dam may be attached to them after it has been installed over the patient's teeth. Other fasteners are on the frame and positioned so that dental tape may be used to tie it in place about a patient's head. The geometry is such that the dental dam does not restrict either the working or the visible area of the patient's mouth.

4 Claims, 7 Drawing Figures

U.S. Patent  Apr. 23, 1985  4,512,742
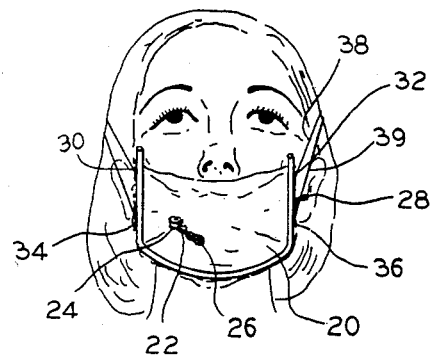
FIG.1
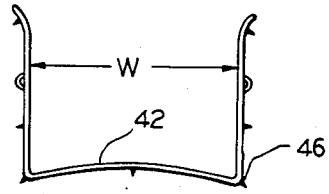
FIG.2
(PRIOR ART)
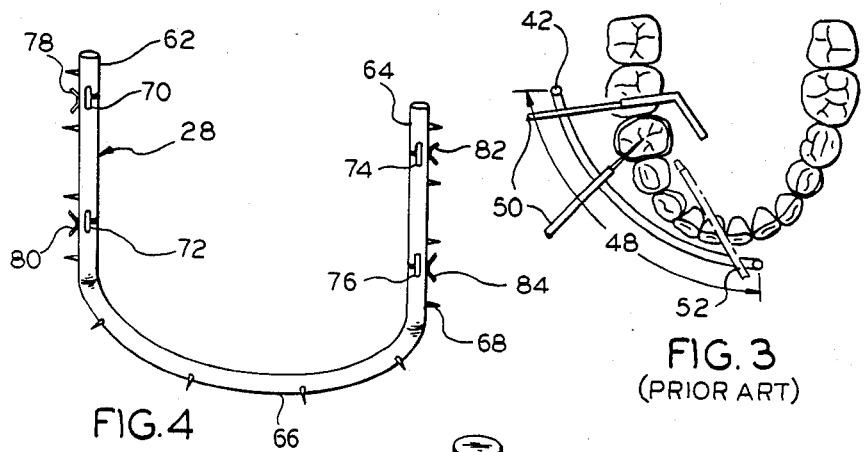
FIG.4
FIG.3
(PRIOR ART)
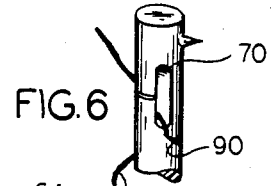
FIG.6
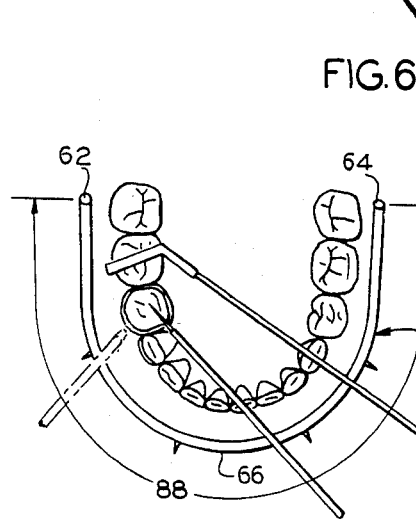
FIG.5
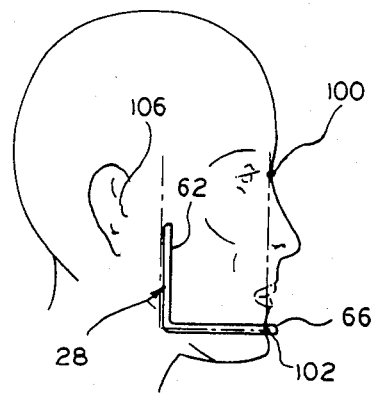
FIG.7

HOLDER FOR RUBBER DENTAL DAM

This is a continuation of application Ser. No. 790,567, filed Apr. 25, 1977, now U.S. Pat. No. 4,215,477, issued Aug. 5, 1980.

This invention relates to dental appliances and more particularly to frame holders for dental dams.

The rubber dam was introduced into dentistry about 1864, in order to ensure complete dryness and cleanliness of the teeth. More particularly, a rubber dam is used to isolate a tooth or the individual teeth being treated. It eliminates saliva from the location of treatment and guards against contamination, because the cavity preparation is initiated and completed without contact by or contamination from the fluids of the mouth. It also protects the patient from the possibility of aspirating or swallowing debris associated with preparation and restoration of the tooth. It retracts the lips, cheeks, tongue, and the marginal tissue to a mild degree, thereby providing better access and vision and protecting the soft tissues from medications that may be irritating or distasteful. The dentist is afforded some degree of protection from infectious conditions that may be present in the patient's mouth.

Heretofore, rubber dams have been held in place by a number of different devices, including frames, harnesses, and the like. The frames which have been used heretofore are designed to stand upright alongside of the mouth. In one method of application, a sheet of rubber is first stretched over and hooked on to the frame. Then the frame is positioned in front of part of the mouth and held in place by one or more straps or another harness which passes behind the head. The rubber dam may also be applied to the teeth first, then stretched to fit the frame.

A difficulty with the prior art frames is that they have tended to restrict the arcuate field over which the dentist and dental assistants may work. Moreover, whether used with or without the prior art frames, the cloth or "Velcro" straps behind the head are transferred from patient to patient, thereby carrying germs, oils, and the like, from patient to patient. The straps have been difficult to attach, often requiring the aid of an assistant. Also, the straps may tend to disarray the patient's coiffure.

Regardless of which method is used, the resulting structure usually presses uncomfortably against the patient's facial tissues. The upper lip and corners of the patient's mouth must be lubricated to prevent chafing. The patient's eyes might be injured unless extreme care is taken. This is especially true if either the dam or harness is stretched so that it could snap, if it breaks loose.

Accordingly, an object of the invention is to provide new and improved means for and methods of holding dental dams. Here an object is to provide dental dam frames which do not restrict the frontal area from which a dentist, or assistant, can work on a patient's teeth.

Another object of the invention is to provide means for and methods of installing dental dams which may be used by one person, without requiring the assitance of a second person.

Still another object of the invention is to provide dental dams which are more comfortable for the patient.

Yet another object is to provide a completely sanitary dental dam support system which cannot transfer any germs, oils, or the like, from patient to patient.

A further object of the invention is to provide improved processes and procedures for installing dental dams, whereby both the dentist and patient enjoy a greater degree of convenience and comfort.

In keeping with an aspect of the invention, these and other objects are accomplished by a facial frame which at least partially surrounds a greater arcuate portion of the patient's face, as compared to the portion surrounded heretofore. The frame includes a plurality of fasteners for attaching thereto an elastic dental dam. These fasteners are oriented so that the dam may be attached to the frame after the dam has been installed over the teeth. Other fasteners are integrally built on to the frame so that it may be tied in place about the patient's head, preferably by means of disposable dental tape. The geometry of the frame is such that the dental dam does not restrict either the working or the visible area of the patient's mouth.

A preferred embodiment of the present invention may be understood best from the attached drawings, wherein:

FIG. 1 is a pictorial representation of a patient with the inventive dental dam installed;

FIG. 2 is a perspective view of a prior art frame for supporting a dental dam;

FIG. 3 schematically indicates how the prior art frame of FIG. 2 creates problems by restricting the working and visual area for both a dentist and a dental assistant;

FIG. 4 is a perspective view of the inventive frame;

FIG. 5 schematically indicates how the invention provides an improved field of work and vision as compared to the prior art frame of FIGS. 2 and 3;

FIG. 6 illustrates an alternative method of anchoring dental tape used to hold the inventive frame in place; and FIG. 7 pictorially shows both the skull and facial tissues of a patient in order to illustrate the preferred location of the inventive dental dam frame with respect to recognized index points on a skull.

The dental dam 20 is conventionally a thin sheet of rubber used for keeping a patient's teeth clean and dry while they are being cut, filled or otherwise repaired. By known techniques, small holes are first punched into the sheet of rubber at the relative location of each tooth (e.g., at 22) that is to project through and be exposed to view when the dam 20 is in place. To install the dam, the dentist places each hole over the corresponding tooth and then see-saws the rubber sheet back and forth over the corresponding teeth. This motion stretches the rubber of the dam so that it tightly surrounds each of the teeth, passing between them, and then down to the gum line.

Next, any suitable known spring clamps 24, 26 are expanded, slipped over appropriate teeth, and relased. The spring contracts under its own internal spring tension and tightly grips the tooth, above the rubber sheet. This holds the rubber sheet and keeps it from being dislodged.

According to the inventive process, the rubber sheet is first installed over the patient's teeth, a rubber napkin is then placed between the sheet and the patient's face and the rubber sheet is attached to a generally U-shaped frame 28. The inventive frame 28 is large enough to span the entire chin area of the patient and to fit on opposite sides of the face. Next, for a right-handed operator, a section of dental tape 38 is attached to one corner 32 of the frame 28, passed behind the patient's head, drawn sufficiently tight and attached to an opposite corner 30 of the frame. Then, a second dental tape 39 is passed behind the head and attached between adjacent corners 36, 34 of the frame, in a similar manner. (Dental tape is a heavy ribbon-like version of conventional waxed dental floss which almost all dentists have on hand, as an office staple.) If a greater amount of contact area is required between the patient's head and the dental tape, it may be threaded through one or more layers of gauze strips to provide a pad at the back of the head.

An advantage of this method of dam installation is that the rubber sheet may be gently hooked onto the frame after a rubber dam napkin is placed between the rubber sheet and the face. As the rubber sheet is pulled taut, the pressure is equalized in all directions. Discomfort to the lower lip and face is greatly reduced due to the contoured support away from the tissues. There is a tendency for the rubber sheet to be better fitted to the individual variations in facial contours with less stretching of tissues because the sheet is hooked over the frame before the retraction is obtained.

The two upright members of the frame are equally spaced on opposite sides of the face, along vertical lines falling between the ears and the corners of the mouth. The tension in the taut rubber sheet, pulling against the head bands 38, 39, holds the frame 28 in a stable and secure position. Therefore, the dentist may rest a finger against the frame for greater security and stability while working on a patient's teeth.

The nature of the improved frame will become more apparent from a comparison and contrast with the dam holding devices that were used heretofore. The prior art method which incorporated frames similar to the frame 42 shown in FIGS. 2, 3, has a generally U-shaped form with a relatively narrow width W which merely covered the restricted portion of the mouth on which the dentist happens to be working. As seen in FIG. 3, the prior art frame 42 subtends an arc 48 which is restricted to about one-third of the total dental arch. Also, the nature of this prior art frame 42 is such that the rubber sheet is often first installed on the frame by hooking it over prongs such as 46 projecting outwardly from frame 42. Then, the dam (with the frame attached) must be worked on, over the teeth. The dentist must be ever watchful to be sure that a part of the frame does not strike the patient's eye. The inventive frame has reduced this problem due to a shorter vertical dimension to the frame, as compared to the vertical dimension of prior devices. Even so, it is easier and quicker to apply these dams that it is to apply the dams which do not have frames and which must be gripped by spring-biased clips on a flexible harness.

After the dam has been fitted over the teeth (FIG. 3), frame 42 is rather loosely suspended in front of the teeth. Since the working area is restricted to the arc 48, the dentist may only insert and use his tools 50 on one side of the frame because the dental assistant also has to hold certain tools 52 in the oral cavity within the opposite side of the frame. Therefore, it is extremely awkward to work in the restricted area of the arc 48, especially when practicing "four-handed" dentistry (where the dentist operates with an assistant) and when doing "quadrant" dentistry (restoring all of one side or an arch, particularly the posterior teeth).

Also, the smaller area of contact between the frame 42 and the patient's face results in imbalanced forces upon the frame. The installation requirements are such that the frame is unstably mounted. Therefore, the dentist cannot rest his finger on the frame 42 with the same degree of stability that he can rest it upon the inventive frame.

Some of the advantages of this prior art type of frame holders are:

1. Easier and faster to apply than strap holders;
2. More tolerable to patients, especially children;
3. Some frames have a "pouch collector" for water and other wastes which must be disposed of when no assistant is present;
4. Readily sterilized frame between patients;
5. Retraction in all directions with no weights necessary;
6. Rubber dam napkin not mandatory;
7. Will not slip off head once it is securely in place.

Disadvantages of these prior art frame holders are:
1. Less stable than strap holders without frames;
2. Strong clamp anchorage required on the teeth themselves, which may be painful to patient;
3. Restriction of dentist's finger movement;
4. Visibility limited for assistant, depending on holder placement;
5. The strap harness for holding the frame in place is not an easily sterilized device.

Common problems with all prior art rubber dam mounting system;
1. Possible injury to patient's eye;
2. Lips and corners of mouth must be lubricated.

The inventive dam holder (FIGS. 4, 5) corrects most of these problems and provides superior results. The new rubber dam support and anchoring design should satisfy a number of conditions including an elimination of the above-cited disadvantages and problems as well as increased usefulness, economy, and ease of use. Sterilization procedures should be easy and patient should be comfortable. The new frame should also incorporate the good qualities of both the frame and frameless systems known to the prior art.

Briefly, according to the invention, the basic construction of the inventive frame (FIGS. 4, 5) entails a plastic (preferably nylon or fluorocarbon resins, such as duPont's TEFLON resin) facially contoured frame, in a generally "U" shape configuration extending from the symphysis to the gonion with the frame contour extending around the mandible and parallel to the facial plane of the face (nasion to pogonion). The plastic material should be sufficiently heat-resistant so that it may be sterilized in an autoclave, and should be substantially rigid, have high strength, and be water-resistant. The frame is preferably made in various sizes, such as small, medium, and large, with most adults falling in the medium range. Since the frame is a one-piece unit, application is easy. A smooth retraction and large working field is created.

In greater detail, the inventive frame 28 (FIGS. 4, 5) includes a pair of uprights 62, 64 interconnected by a facial bow 66 which is generally positioned in front of the chin. A predetermined number of relatively sharp stakes (such as 68) are formed on both of the uprights 62, 64 and on the facial bow 66 of the frame. According to the invention, there are preferably four stakes on each upright and four more on the facial bow; however, another number of stakes may be provided. These stakes are positioned to project outwardly from the frame 28 in locations and at an angle which may be used to hook into and securely hold the rubber dam, without snapping the dentist, patient, or their clothing. Preferably, these stakes are integrally molded into the plastic of the frame itself. The stake points are not sharp enough to scratch a person, but they are sharp enough to easily grasp the rubber sheet.

After the rubber dam has been installed in the patient's mouth, the inventive frame 28 is brought up to a point near the patient's face. The rubber dam is pulled around behind the frame and hooked on over the stakes 68 which grasp the rubber sheet.

A vertically-oriented pair of generally T-shaped slots 70–76 and cleats 78–84 are oppositely disposed on the vertical members 62, 64. Each of the T-shaped slots 70–76 include a horizontal portion which enables a length of dental tape to pass therethrough. Each of the T-shaped slots 70–76 also includes a vertical portion which enables minor adjustments in the vertical positions of the dental tape to accommodate different patient requirements. This way, the relative dental tape frame positions may be adjusted according to head size and shape.

Each of the cleats 78–84 comprises a pair of horns, as shown at 82, 84. Hence, the dental tape which is slipped into slot 70 (for example) may be looped around each of the horns, in turn. The last loop is inverted and pulled tightly to take a bite upon one of the horns. This way, the rubber dam frame 28 may be quickly and easily tied securely to the patient's head by means of disposable dental tape so that no structure is ever transferred from one to another patient's head, except for the frame which may be sterilized.

FIG. 5 is similar to FIG. 3 and shows that the dentist may work over a very wide angle 88, as compared to the relatively narrow work angle 48 of the prior art frame 48.

FIG. 6 shows an alternative embodiment for anchoring the end of the dental tape. Instead of using the cleat 78 shown in FIG. 4, the embodiment of FIG. 6 includes a slot 90 into which the dental tape 92 may be wedged after it is drawn through slot 70, to hold the tape 92 in position.

FIG. 7 shows the desired position of the inventive frame relative to well-known points on the patient's head. In greater detail, the facial plane includes the nasion 100 and the pogonion 102. The upright members 62, 64 of the inventive frame should be parallel to the facial plane and located approximately one-quarter of the distance extending from the ear 106 to the facial plane. In this position, the origin of the upright frame members will be at approximately the gonion.

Those who are skilled in the art will readily perceive how to modify the system. Therefore, the appended claims are to be construed to cover all equivalent structures.

I claim:

1. A human facial frame means for holding a dental dam, said frame means being generally U-shaped with an arcuate bottom frame member with means comprising two upright members, said bottom member being adapted to extend around and in front of a human mandible, said arcuate bottom member being adapted to be wide enough to span the entire chin and mandible area and to fit on opposite sides of a patient's face, the uprights having a relatively short length so that they do not rest on the cheek bone, said arcuate bottom member further being adapted to surround a substantial arcuate portion of a patient's mandible, extending substantially from the molar area on one side to the molar area on the other side of the mandible, said two upright members of the U-shaped frame means being adapted to be positioned on opposite sides of the face and head, the width and angle of the uprights being adapted to cause said uprights to come to rest in a position where the upright members are generally parallel to a facial plane which is defined by the patient's nasion and the pogonion, said two upright members being adapted to be located at positions in the range of approximately one-quarter of the distance extending from the ear toward the facial plane, the origin of the two upright frame members being adapted to be located on opposite sides of the patient's head and over approximately the gonion, the bottom of the U-shaped means being adapted to rest on and pivoted around the pogonion in the front of the chin, the two upright frame members having said relatively short length which is adapted to have a top end which is well below and away from the patient's eyes in the direction of the ears when said uprights are in said resting position, a plurality of outwardly projecting means for securing a dental dam around the periphery of the U-shaped frame means, and means on the frame for adapting it to be anchored in place about a patient's head.

2. A dental dam frame comprising a generally U-shaped bar member having a bottom which is a generally arcuate configuration with an inside span, the center of said bottom being adapted to rest on and pivot about the notch in a patient's chin, said bottom of the bar member being adapted to extend around the outside of the lower dental arch and terminate on substantially opposite ends of the arch in upright posts at points where the posts do not rest against the soft tissue in the area of the cheek bone of the patient, whereby the inside span of said bottom has a length which is adapted to be great enough for the bottom of the bar member to span the entire chin area of said frame to rest on and pivot about the notch at the front of the patient's chin said upright posts being adapted to pass on opposite sides of the patient's face during said pivoting, said frame being adapted to rotate about said pivot and rest in a position wherein said uprights are approximately parallel to the facial plane without exerting substantial pressure on this soft and fleshy parts of the face, and a plurality of fasteners distributed around said frame to secure a dental dam thereto.

3. The frame of either claim 1 or claim 2 wherein said fasteners for securing the dental dam are a plurality of stakes spaced around the frame.

4. The frame of claim 3 wherein said stakes are positioned to secure the rubber dam without snagging the patient or people working around the dam.

* * * * *